United States Patent [19]

Ollinger et al.

[11] 4,263,288
[45] Apr. 21, 1981

[54] ACARICIDAL, INSECTICIDAL, AND NEMATOCIDAL PHOSPHORAMIDOTHIOATES

[75] Inventors: Janet Ollinger, North Wales; Horst O. Bayer, Levittown, both of Pa.

[73] Assignee: Rohm and Haas Company, Philadelphia, Pa.

[21] Appl. No.: 964,214

[22] Filed: Nov. 27, 1978

Related U.S. Application Data

[63] Continuation-in-part of Ser. No. 866,597, Jan. 3, 1978, abandoned.

[51] Int. Cl.³ .................... C07F 9/24; A01N 57/30
[52] U.S. Cl. .................... 424/210; 260/347.2; 260/940; 260/943; 260/944; 424/203; 424/211
[58] Field of Search ............... 260/944, 923, 940, 943, 260/347.2; 424/211, 210, 203

[56] References Cited

U.S. PATENT DOCUMENTS

| | | | |
|---|---|---|---|
| 3,758,645 | 9/1973 | Leber et al. | 260/973 |
| 3,925,517 | 12/1975 | Pissiotas et al. | 260/944 |
| 3,962,305 | 6/1976 | Pallos | 260/944 |

FOREIGN PATENT DOCUMENTS 1080450  8/1967  United Kingdom ............... 260/944

*Primary Examiner*—Anton H. Sutto
*Attorney, Agent, or Firm*—Lester E. Johnson

[57] ABSTRACT

This invention relates to novel phosphoramidothioates of the formula:

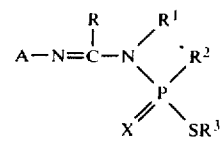

wherein
A is optionally substituted $(C_6-C_{10})$ aryl;
R is hydrogen or $(C_1-C_6)$ alkyl;
$R^1$ is
(a) optionally substituted $(C_1-C_6)$ alkyl,
(b) $(C_3-C_8)$ cycloalkyl,
(c) optionally substituted $(C_3-C_6)$ alkenyl,
(d) $(C_3-C_6)$ alkynyl, or
(e) optionally substituted $(C_7-C_{11})$ aralkyl;
$R^2$ is
(a) $(C_1-C_6)$ alkylthio,
(b) $(C_6-C_{10})$ aryloxy, or
(c) NZ'Z''; wherein
Z' is hydrogen or $(C_1-C_6)$ alkyl; and
Z'' is hydrogen, $(C_1-C_6)$ alkyl, $(C_3-C_6)$ alkenyl, di($C_1-C_3$) alkylamino, 2-ethylthioethyl, 2-methoxyethyl or $(C_1-C_4)$ alkoxycarbonylalkyl $(C_1-C_4)$;
$R^3$ is unsubstituted $(C_1-C_6)$ alkyl; and
X is oxygen or sulfur;

to compositions containing them and to methods of using them to control certain harmful pests.

27 Claims, No Drawings

ACARICIDAL, INSECTICIDAL, AND NEMATOCIDAL PHOSPHORAMIDOTHIOATES

This application is a continuation-in-part of application Ser. No. 866,597 filed Jan. 3, 1978, now abandoned.

This invention relates to novel phosphoramidothioates, to compositions containing them, and to methods of using them to control a variety of harmful pests.

The novel compounds of this invention can be represented by the formula $$A-N=C(R)-N(R^1)(R^2)-P(=X)(SR^3)$$

wherein

A is an unsubstituted ($C_6-C_{10}$) aryl group preferably an unsubstituted phenyl group; or a ($C_6-C_{10}$) aryl group substituted with up to three substituents selected from the group consisting of cyano, nitro, halogen, ($C_1-C_6$) alkyl, ($C_1-C_6$) alkoxy, ($C_1-C_6$) alkylthio, acetoxy, trifluoromethyl, ($C_1-C_6$) alkylaminocarbonyl, di-($C_1-C_6$) alkylaminocarbonyl, halo ($C_1-C_6$) alkyl, ($C_1-C_6$) alkylsulfinyl, ($C_1-C_6$) alkylsulfonyl, ($C_6-C_{10}$) aryloxy, ($C_6-C_{10}$) arylthio, arylsulfinyl, arylsulfonyl, ($C_1-C_6$) alkylcarbonyl or acetyl, preferably a phenyl group substituted with up to three substituents selected from the group consisting of cyano, nitro, halogen, ($C_1-C_4$) alkyl, ($C_1-C_4$) alkoxy, ($C_1-C_4$) alkylthio, acetoxy, trifluoromethyl, ($C_1-C_4$) alkylsulfinyl, ($C_1-C_4$) alkylsulfonyl, phenoxy and acetyl, more preferably with the substituents selected from the group consisting of cyano, chloro, fluoro, bromo, methyl, ethyl, methylthio, acetoxy, trifluoromethyl, methylsulfinyl, methylsulfonyl, acetyl, and phenoxy; most preferably with up to two substituents selected from the group consisting of methyl, chloro, cyano, methoxy, methylthio acetyl and phenoxy;

R is a hydrogen atom or an unsubstituted ($C_1-C_6$) alkyl group; preferably a hydrogen atom or a ($C_1-C_4$) alkyl group, more preferably a hydrogen atom;

$R^1$ is (a) an unsubstituted ($C_1-C_6$) alkyl group, or a ($C_1-C_6$) alkyl group substituted with up to one substituent selected from the group consisting of cyano, furyl, ($C_1-C_6$) alkoxy, ($C_1-C_6$) alkylthio, ($C_1-C_6$) alkylsulfinyl, ($C_1-C_6$) alkylsulfonyl, ($C_3-C_6$) alkenyloxy, ($C_3-C_6$) alkenyloxycarbonyl, ($C_1-C_6$) alkylcarbonyl, ($C_1-C_6$) alkoxycarbonyl, ($C_1-C_6$) alkylcarbonyloxy, mono- or di($C_1-C_6$) alkylaminocarbonyl, di-($C_1-C_6$) alkylamino, ($C_6-C_{10}$) aryloxy, ($C_6-C_{10}$)arylthio, ($C_6-C_{10}$)akylsulfinyl, ($C_6-C_{10}$) arylsulfonyl, ($C_6-C_{10}$) arylcarbonyl, ($C_6-C_{10}$)aryloxycarbonyl, ($C_6-C_{10}$) arylcarbonyloxy, or ($C_6-C_{10}$) arylaminocarbonyl; preferably an unsubstituted ($C_1-C_4$) alkyl group, or a ($C_1-C_4$) alkyl group substituted with one substituent selected from the group consisting of cyano, ($C_1-C_4$) alkoxy, ($C_1-C_4$) alkylthio, ($C_1-C_4$) alkylsulfinyl, ($C_1-C_4$) alkylsulfonyl, ($C_1-C_4$) alkylcarbonyl, ($C_1-C_4$) alkoxycarbonyl, ($C_1-C_4$) alkylcarbonyloxy, mono- or di-($C_1-C_4$) alkylaminocarbonyl, di-($C_1-C_4$) alkylamino, ($C_3-C_4$) alkenyloxy, ($C_3-C_4$) alkenyloxycarbonyl, phenoxy, phenylthio, phenylsulfinyl, phenylsulfonyl, phenylcarbonyl, phenyoxycarbonyl, phenylcarbonyloxy, and phenylaminocarbonyl; more preferably an unsubstituted ($C_1-C_4$) alkyl group;

(b) an unsubstituted ($C_3-C_8$) preferably ($C_5-C_7$) cycloalkyl group;

(c) an unsubstituted ($C_3-C_6$) alkenyl group or a ($C_3-C_6$) alkenyl group with up to two substituents selected from the group consisting of cyano, halogen, ($C_1-C_6$) alkoxycarbonyl, and an unsubstituted ($C_6-C_{10}$) aryl group substituted with up to three substituents selected from the group consisting of cyano, nitro, halogen, ($C_1-C_6$) alkyl, ($C_1-C_6$) alkoxy, ($C_1-C_6$) alkylthio, ($C_1-C_6$) alkylaminocarbonyl, di-($C_1-C_6$) alkylaminocarbonyl, and halo ($C_1-C_6$) alkyl; preferably a ($C_3-C_4$) alkenyl group substituted with up to two substituents selected from the group consisting of cyano, halogen, ($C_1-C_3$) alkoxycarbonyl, and unsubstituted phenyl, more preferably an unsubstituted ($C_3-C_4$) alkenyl;

(d) an unsubstituted ($C_3-C_6$) alkynyl group;

(e) an unsubstituted aralkyl group of up to 11 carbon atoms, or an aralkyl group of up to 11 carbon atoms the aryl portion of which is substituted with up to three substituents selected from the group consisting of cyano, nitro, halogen, ($C_1-C_6$) alkyl, ($C_1-C_6$) alkoxy, ($C_1-C_6$) alkylthio, ($C_1-C_6$) alkylaminocarbonyl, di-($C_1-C_6$) alkylaminocarbonyl and halo ($C_1-C_6$) alkyl; preferably an unsubstituted benzyl or phenethyl group, or a benzyl or phenethyl group substituted with up to three substituents selected from the group consisting of cyano, nitro, halogen, ($C_1-C_4$) alkyl, ($C_1-C_4$) alkoxy, ($C_1-C_4$) alkylthio, ($C_1-C_4$) alkylaminocarbonyl, di-($C_1-C_4$) alkylaminocarbonyl and halo ($C_1-C_6$) alkyl, more preferably unsubstituted benzyl;

$R^2$ is (a) ($C_1-C_6$) alkylthio, preferably ($C_3-C_4$)alkylthio;

(b) ($C_6-C_{10}$) aryloxy, preferably phenoxy or 4-nitrophenoxy;

(c) a group of the formula NZ'Z'' wherein

Z' is hydrogen or ($C_1-C_6$) alkyl, preferably hydrogen or methyl, most preferably hydrogen; and Z'' is hydrogen, ($C_1-C_6$) alkyl, ($C_3-C_6$) alkenyl, di-($C_1-C_3$) alkylamino, 2-ethylthioethyl, 2-methoxyethyl or ($C_1-C_4$) alkoxycarbonylalkyl($C_1-C_4$), preferably methyl or ethyl, most preferably methyl, $R^3$ is an unsubstituted ($C_1-C_6$), preferably ($C_3-C_4$) alkyl group; and X is an oxygen or sulfur, preferably oxygen atom;

As used in the specification and claims, the terms alkyl, alkenyl and alkynyl are meant to include branched as well as straight chain alkyl, alkenyl and alkynyl groups. Representative examples of such groups include methyl, ethyl, propyl, isopropyl, sec-butyl, isobutyl, tert-butyl, pentyl, neopentyl, hexyl, allyl, 2-butenyl, 3-methyl-1-pentenyl, 3-hexenyl, propynyl, 1-pentynyl, 4-methyl-1-pentynyl, hexynyl, and the like.

The term optionally substituted means substituted or unsubstituted.

By a substituted ($C_6-C_{10}$) aryl group, as used in the specification and claims, is meant an aryl group such as phenyl or naphthyl, substituted with one or more, but preferably with one to three, substituents selected from the group consisting of alkyl, halogen, haloalkyl, alkoxy, alkylsulfonyl, alkylthio, alkylsulfinyl, nitro, cyano, alkoxycarbonyl, dialkylamino, alkylcarbonyl, dialkylaminocarbonyl, and the like, wherein each alkyl moiety is straight or branched chain and contains from 1 to 6, preferably from 1 to 3 carbon atoms, and aryl, aryloxy, arylthio, arylsulfinyl, arylsulfonyl and the like, wherein the aryl ring contains from 6 to 10, preferably 6, carbon atoms, e.g., phenyl, phenoxy, phenylthio, and the like. The preferred aryl substituents are halogen, preferably chlorine; ($C_1$–$C_4$) alkyl, preferably methyl; ($C_1$–$C_4$) alkoxy, preferably methoxy, and ($C_1$–$C_4$) alkylthio, preferably methylthio, cyano, phenoxy, and ($C_1$–$C_4$) alkylcarbonyl, preferably acetyl;

By a substituted alkyl group as used in the specification and claims is meant an alkyl group, substituted with one substituent selected from the group consisting of cyano, nitro, furyl, alkoxy, alkylthio, alkylsulfinyl, alkylsulfonyl, alkylcarbonyl, alkoxycarbonyl, alkylcarbonyloxy, mono- or di-alkylaminocarbonyl, and the like, wherein each alkyl moiety is straight or branched chain, and contains from 1 to 6, preferably from 1 to 3, carbon atoms; alkenyloxy and alkenyloxycarbonyl wherein the alkenyl moiety contains from 3 to 6 preferably from 3 to 4 carbon atoms; and aryloxy, arylthio, arylsulfinyl, arylsulfonyl, arylcarbonyl, aryloxycarbonyl, arylcarbonyloxy, arylaminocarbonyl, and the like, wherein the aryl ring contains from 6 to 10 carbon atoms, preferably a phenyl ring, which is optionally substituted (but preferably unsubstituted) with substituents such as defined for substituted ($C_6$–$C_{10}$) aryl above. The preferred alkyl substituents are alkoxycarbonyl, alkoxy, alkylthio, phenylthio and cyano.

By a substituted alkenyl group, as used in the specification and claims, is meant an alkenyl group such as an allyl group, or the like substituted with one or more, preferably up to two, substituents selected from the group consisting of cyano, halogen preferably chlorine; alkoxy, preferably methoxy; alkylcarbonyl, wherein the alkyl moiety is straight or branched chain and contains from 1 to 6, preferably from 1 to 3 carbon atoms, or an optionally substituted ($C_6$–$C_{10}$) aryl group, preferably an unsubstituted phenyl group.

By a substituted aralkyl group is meant an aralkyl group e.g., benzyl, phenethyl, 3-phenyl-1-methylpropyl, etc., substituted with one or more, but preferably with one to three substituents selected from the group of substituents defined for substituted ($C_6$–$C_{10}$) aryl above.

In the definition of the terms arylthio and aryloxy, the aryl moiety contains from 6 to 10 carbon atoms, preferably a phenyl ring, optionally substituted (but preferably unsubstituted) with substituents such as defined for substituted ($C_6$–$C_{10}$) aryl above.

In a preferred embodiment of the invention the A substituent in Formula I has the formula:

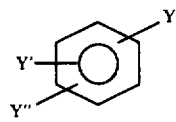

(II)

wherein Y, Y' and Y" are independently a hydrogen atom, a cyano group, a halogen atom, preferably a chlorine atom; a ($C_1$–$C_4$) alkyl group, preferably a methyl group; a ($C_1$–$C_4$) alkoxy, preferably a methoxy group; a ($C_1$–$C_4$) alkylthio group, preferably a methylthio group; an acetyl group, a trifluoromethyl group, a ($C_1$–$C_4$) alkylsulfinyl group, preferably a methylsulfinyl group; a ($C_1$–$C_4$) alkylsulfonyl group, preferably a methylsulfonyl group; and phenoxy.

The most preferred compounds of this invention possess especially enhanced nematocidal, fungicidal and arthropodicidal, particularly acaricidal and insecticidal activity. They can be represented by the formula:

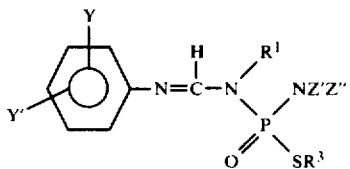

wherein $R^1$ is a methyl group, an ethyl group, an unsubstituted ($C_5$–$C_7$)cycloalkyl group, an unsubstituted ($C_3$–$C_4$)alkenyl group, an unsubstituted ($C_3$–$C_4$)alkynyl group, a benzyl group or a ($C_1$–$C_4$)alkyl group substituted with 2-methoxyethyl, 2-methylthioethyl, 2-(ethoxycarbonyl)ethyl, or 1-(ethoxycarbonyl)ethyl;

$R^3$ is a ($C_3$–$C_4$) alkyl group;

Z' is a hydrogen atom;

Z" is a ($C_1$–$C_4$) alkyl group preferably an ethyl or methyl group,

Y, and Y' are independently hydrogen atoms, groups, methyl groups, or chlorine atoms an acetyl group, a methylthio group, a methoxy group, a cyano group, or a phenoxy group.

Particular preferred compounds of the invention have the following formulae:

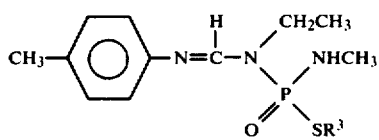

wherein $R^3$ is $C_3H_7$-n, $C_4H_9$-s, or $C_4H_9$-i;

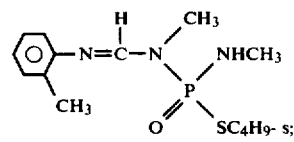

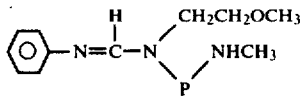

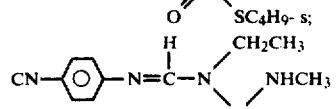

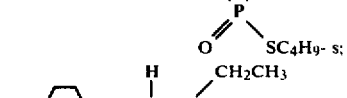

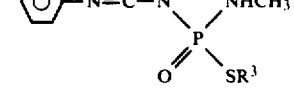

wherein $R^3$ is $C_3H_7$-n, $C_4H_9$-s, $C_4H_9$-i.

Typical examples of compounds within the scope of this invention include the following:

N-Butyl N'-ethyl S-(1-methylpropyl) N-(phenylimino)-methyl phosphorodiamidothioate N-Methyl N'-methyl N-[1-(2,4-dimethylphenylimino)ethyl]S-propyl phosphorodiamidothioate N'-Ethyl N-[(4-nitrophenylimino)methyl]N-propyl S-propyl phosphorodiamidothioate N-Cyclohexyl N'-methyl N-(phenylimino)methyl S-propyl phosphorodiamidothioate N-Methyl N'-methyl N-[1-(2-methylphenylimino)pentyl]S-(1-methylpropyl) phosphorodiamidothioate N-[(4-Cyanophenylimino)methyl]N-ethylthiomethyl N'-methyl S-(2-methylpropyl) phosphorodiamidothioate N-[1-(2,4,6-Trichlorophenylimino)ethyl]N'-methyl N-(2-methoxyethyl) S-(1-methylpropyl) phosphorodiamidothioate N'-Ethyl N-methyl N-[(4-methylthiophenylimino)methyl] S-propyl phosphorodiamidothioate N-[(2-Chlorophenylimino)methyl] N-(2-cyanoethyl) N'-ethyl S-(2-methylpropyl) phosphorodiamidothioate S-Butyl N-(2-phenylthioethyl) N',N'-dimethyl N-[(2-methyl-4-nitrophenylimino)methyl] phosphorodiamidothioate N-[(4-Bromophenylimino)methyl] N-(3-chloro-2-propenyl) N', N'-diethyl S-propyl phosphorodiamidothioate N-[(2-Ethoxycarbonylphenylimino)methyl] N'-methyl S-(2-methylpropyl) N-propyl phosphorodiamidothioate N-Ethyl N-[(4-diethylaminocarbonylphenylimino)methyl] N'-methyl S-propyl phosphorodiamidothioate N'-Ethyl S-hexyl N-(3-methylsulfonylpropyl) N-[(4-methylphenylimino)methyl]phosphorodiamidothioate N-[(4-Methoxy-2-methylphenylimino)methyl]N-methyl S-(2-methylpropyl) S-propyl phosphoramidodithioate N-[(4-Chloro-2-methylphenylimino)methyl] S-(1-methylpropyl) S-(2-methylpropyl) N-(2-phenoxyethyl) phosphoramidodithioate N-[1-(2-Cyanophenylimino)ethyl] S,S-di(1-methylpropyl) N-phenylmethyl phosphoramidodithioate N-(2-Butenyl) S,S-di(2-methylpropyl) N-[(4-methylthiophenylimino)methyl]phosphoramidodithioate N-[(4-Methoxycarbonylphenylimino)methyl] N-methyl S,S-dipropyl phosphoramidodithioate N-Benzenesulfonylmethyl N-(phenylimino)methyl S,S-dipropyl phosphoramidodithioate S-Ethyl N-methyl N-[1-(4-methylthiophenylimino)ethyl] S-propyl phosphoramidodithioate N-Ethylcarbonylmethyl N-[(2-phenoxyphenylimino)methyl] O-phenyl S-propyl phosphoramidothioate N-Ethyl N-[1-(phenylimino)ethyl] O-phenyl S-propyl phosphoramidothioate N-Methoxycarbonylmethyl N-[1-(4-methylphenylimino)ethyl] S-(1-methylpropyl) O-phenyl phosphoramidothioate N-[1-(4-Chlorophenylimino)ethyl] N-methylaminocarbonylmethyl S-(1-methylethyl) O-phenyl phosphoramidothioate N-[2-Chloro-4-methylsulfonylphenylimino)methyl] S-ethyl N-methyl O-phenyl phosphoramidothioate N-(2-Butynyl) N-[(4-methylcarbonylphenylimino)methyl] O-(4-nitrophenyl) S-propyl phosphoramidothioate N-[2-(Dimethylaminocarbonyl)ethyl]S-(2-methylpropyl) O-(4-nitrophenyl) N-(phenylimino)methyl phosphoramidothioate N-Ethyl N-[(2-methylphenylimino)methyl] S-(1-methylpropyl) O-(4-nitrophenyl) phosphoramidothioate S-Ethyl N-[(4-methoxycarbonylphenylimino)methyl] N-methyl O-(4-nitrophenyl) phosphoramidothioate N-(2-Cyanoethyl) N-[(4-dimethylaminocarbonylphenylimino) methyl] S-(2-methylpropyl) O-(4-nitrophenyl) phosphoramidothioate The compounds of the present invention can be prepared by a variety of methods. One method involves reacting an amidine with a phosphorochloridothioate or phosphorochloridodithioate in the presence of an acid binding agent. The general reaction can be represented by the following equation:

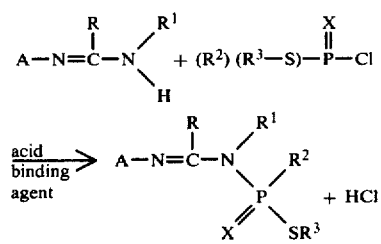

wherein A, R, $R^1$, $R^2$, $R^3$, and X are as defined for Formula I.

Another method involves reacting an amidine with S-alkyl phosphorodichloridothioate in the presence of an acid binding agent (or strong acid scavenger), followed by the addition of $HR^2$ and an acid binding agent. The general reaction can be represented by the following equation:

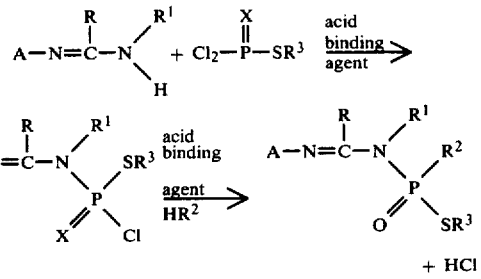

Representative acid binding agents include tertiary amines such as trialkylamines and dialkylanilines, and inorganic bases such as carbonates and bicarbonates of alkali and alkaline earth metals. Generally, a substantially equimolar ratio of reactants is preferred. While not required, the reaction is advantageously carried out in the presence of an inert organic solvent such as an ether, aromatic hydrocarbon, halogenated aromatic hydrocarbon, aliphatic hydrocarbon, aliphatic ketone, aliphatic nitrile, and the like, or mixtures thereof. Suitable solvents include, for example, ethyl ether, dioxane, tetrahydrofuran, benzene, toluene, chlorobenzene, heptane, methylethyl ketone, acetone, acetonitrile, and the like. The reaction is generally conducted in a temperature range of about −10° to 100° C. or more, and preferably in the range of about 0° to about 60° C.

All of the starting materials used in the preparation of the compounds of this invention are known compounds or are easily prepared by adaptations of known routes. The formamidine starting materials are prepared for example by condensation of an aniline with an N-alkyl formamide. (U.S. Pat. No. 3,502,720, Belgian Pat. No. 771,792, South African Pat. No. 732,129.) The S-alkyl phosphorodichloridothioates are prepared by the method described in U.S. Pat. No. 4,056,581.

The following examples are given by way of illustration, and are not to be considered as limitations of the present invention.

EXAMPLE 1

N,N'-Dimethyl S-(1-methylpropyl) N-[(2-methylphenylimino)methyl] phosphorodiamidothioate A solution of N-methyl S-(1-methylpropyl) phosphoramidochloridothioate, 2.5 g. (0.014 mole), in 10 ml. of tetrahydrofuran (THF) is added dropwise to an ice-cooled solution of N-methyl-N'-(2-methylphenyl) formamidine, 2.0 g. (0.014 mole), and triethylamine, 1.36 g. (0.014 mole), in 25 ml of THF. The reaction is stirred 1 hour at room temperature, diluted with 50 ml. of ether, filtered to remove the triethylamine hydrochloride, and evaporated. The residue is diluted with 150 ml. of ether/hexane (2:1), which enables the precipitation of additional triethylamine hydrochloride, isolated by filtration through super cel. Evaporation of the filtrate gives 3.7 g. of yellow oil which is chromatographed on 35 g. of Biosil A. Elution with 550 ml. of 10% ether in benzene (discarding the first 200 ml) gives 1.7 g. of product.

EXAMPLE 2

N'-Methyl S-(1-methypropyl) N-(phenylimino)methyl N-(2-propenyl) phosphorodiamidothioate A solution of N-methyl S-(1-methylpropyl) phosphoramidochloridothioate, 2.96 g. (0.016 mole), in 15 ml. of THF is added dropwise to an ice-cooled solution of N-allyl-N'-phenyl formamidine, 2.5 g. (0.016 mole) and triethylamine, 1.58 g. (0.016 mole) in 30 ml. of THF. The reaction is stirred 1 hour at room temperature, diluted with 50 ml. of ether, and evaporated to give an oil. The oil is diluted with 200 ml. of ether/hexane (2:1) in order to precipitate additional triethylamine hydrochloride, isolated by filtration through super cel. Evaporation of the filtrate gives 4.5 g. of orange oil, which is chromatographed on 40 g. of Biosil A. Elution with 900 ml. of benzene gives 1.5 g. of product.

EXAMPLE 3

N-(2-Cyanoethyl) N'-methyl S-(1-methylpropyl) N-[(4-methylphenylimino)methyl] phosphorodiamidothioate A solution of N-methyl S-(1-methylpropyl) phosphoramidochloridothioate, 2.15 g. (0.011 mole) in 10 ml. of THF is added dropwise to an ice-cooled solution of N-(2-cyanoethyl)-N'-(4-methylphenyl) formamidine, 2.0 g. (0.011 mole) and triethylamine, 1.08 g. (0.011 mole) in 20 ml. of THF. The reaction is stirred 1 hour at room temperature, then filtered to remove triethylamine hydrochloride, and the filtration was evaporated. The residue is diluted with 110 ml. of ether/THF (10:1) to precipitate additional triethylamine hydrochloride, which is removed by filtration through super cel. Evaporation of the solvent gives 3.2 g. of yellow oil, which is chromatographed on 20 g. of Biosil A. Elution with 450 ml. of 20% ether in benzene gives 1.2 g. of product.

The following examples are prepared in an analogous manner. (Examples 4–26)

(4) N,N'-Dimethyl N-[(2-methylphenylimino)methyl] S-propyl phosphorodiamidothioate, (5) N-[4-Chloro-2-methylphenylimino)methyl] N,N'-dimethyl S-(1-methylpropyl) phosphorodiamidothioate, (6) N-Methyl N-(phenylimino)methyl N', S-dipropyl phosphorodiamidothioate, (7) N-[4-Chlorophenylimino)methyl] N-(2-propenyl) N',S-dipropyl phosphorodiamidothioate, (8) N,N'-Dimethyl S-(1-methylpropyl) N-(phenylimino)methyl phosphorodiamidothioate, (9) N'-Methyl N-[(4-methylphenylimino)methyl]S-(1-methylpropyl) N-(2-propenyl) phosphorodiamidothioate,

(10) N-Ethyl N-[(4-methylphenylimino)methyl] S-(1-methylpropyl) N'-propyl phosphorodiamidothioate,

(11) N-Methyl N'-(1-methylethyl) N-[(4-methylphenylimino)methyl] S-propyl phosphorodiamidothioate,

(12) N-[(4-Chlorophenylimino)methyl] N-ethyl N'-(1-methyl ethyl) S-(1-methylpropyl)phosphoramidothioate,

(13) N-Ethyl N'-methyl N-[(4-methylphenylimino)methyl] S-(1-methylpropyl) phosphorodiamidothioate,

(14) N-[(3-Chlorophenylimino)methyl] N-ethyl N'-methyl S-(1-methylpropyl) phosphorodiamidothioate,

(15) N-(2-Cyanoethyl) N'-methyl N-[(2-methylphenylimino)methyl] S-(1-methylpropyl) phosphorodiamidothioate,

(16) N,N'-Dimethyl N-[1-(phenylimino)ethyl] S-(1-methylpropyl) phosphorodiamidothioate,

(17) N-(2-Cyanoethyl) N'-methyl S-(1-methylpropyl) N-(phenylimino)methyl phosphorodiamidothioate,

(18) N'-Methyl N-[(4-methylphenylimino)methyl] S-(1-methylpropyl) N-propyl phosphorodiamidothioate,

(19) N-[(4-Chlorophenylimino)methyl] N'-methyl S-(1-methylpropyl) N-(2-propenyl) phosphorodiamidothioate,

(20) N-Ethyl N-[(4-methylphenylimino)methyl] S-(1-methylpropyl) N'-(2-propenyl) phosphorodiamidothioate,

(21) N-[(4-Methylphenylimino)methyl] N-(2-propenyl) N',S-dipropyl phosphorodiamidothioate,

(22) N'-Ethyl N-methyl S-(1-methylpropyl) N-(phenylimino) methyl phosphorodiamidothioate,

(23) N, N,N'-Trimethyl S-(1-methylpropyl) N-(phenylimino) methyl phosphorodiamidothioate,

(24) N, N',N'-Trimethyl S-(1-methylpropyl) N-[1-(phenylimino)ethyl] phosphorodiamidothioate,

(25) N, N', N'-Trimethyl N-[1-(phenylimino)ethyl] S-propyl phosporodiamidothioate,

EXAMPLE 26

N,N'-Diethyl S-(1-methylpropyl) N-(phenylimino)methyl phosphorodiamidothioate

A solution of N-ethyl-N'-phenyl formamidine, 6.0 g. (0.04 mole) and triethylamine, 3.84 g. (0.04 mole) in 80 ml. of THF is added dropwise to an ice-cooled solution of S-(1-methylpropyl) phosphorodichloridothioate, 7.8 g. (0.04 mole), in 100 ml. of THF. The reaction is stirred 3 hours at room temperature. A solution of triethylamine, 3.84 g., (0.04 mole) and ethylamine, 1.82 g. (0.04 mole), in 50 ml. of THF is added dropwise. The reaction is stirred 2 hours at room temperature, diluted with 200 ml. of ether, filtered to remove the triethylamine hydrochloride, filtered, and evaporated. Crystals form which are recrystallized from 100 ml of hexane/ether (3:1) gives a total of 5 g. of product, m.p. 87°–89° C.

The following examples are prepared in an analogous manner. Oils are purified by column chromatography.

(27) N,N'-Diethyl N-[(4-methylphenylimino)methyl] S-(1-methylpropyl) phosphorodiamidothioate,

(28) N-Ethyl N'-methyl N-(phenylimino)methyl S-propyl phosphorodiamidothioate,

(29) N,N'-Diethyl N-(phenylimino)methyl S-propyl phosphorodiamidothioate,

(30) N-Ethyl N'-methyl S-(1-methylpropyl) N-(phenylimino) methyl phosphorodiamidothioate,

(31) N'-Ethyl N-methyl N-(phenylimino)methyl S-propyl phosphorodiamidothioate,

(32) N,N'-Dimethyl N-(phenylimino)methyl S-propyl phosphorodiamidothioate,

(33) N-Ethyl N',N'-dimethyl N-[(4-methylphenylimino)methyl] S-(1-methylpropyl) phosphorodiamidothioate,

(34) N-Ethyl N'-methyl N-[(2-methylphenylimino)methyl] S-(1-methylpropyl) phosphorodiamidothioate,

(35) N,N'-Diethyl N-[(2-methylphenylimino)methyl] S-(1-methylpropyl) phosphorodiamidothioate,

(36) N'-Methyl N-(phenylimino)methyl N-(2-propenyl) S-propyl phosphorodiamidothioate,

(37) N-Ethyl N'-methyl S-(2-methylpropyl) N-(phenylimino) methyl phosphorodiamidothioate,

(38) N'-Ethyl N-(phenylimino)methyl N-(2-propenyl) S-(1-methylpropyl) phosphorodiamidothioate,

(39) N-Ethyl N-[(4-methoxyphenylimino)methyl] N'-methyl S-(1-methylpropyl) phosphorodiamidothioate,

(40) N-Ethyl N-[(4-methoxyphenylimino)methyl] N'-methyl S-(2-methylpropyl) phosphorodiamidothioate,

(41) N-Ethyl N'-methyl N-[(4-methylphenylimino)methyl] S-propyl phosphorodiamidothioate,

(42) N-[(2,4-Dichlorophenylimino)methyl] N-ethyl N'-methyl S-(1-methylpropyl) phosphorodiamidothioate,

(43) N-[(3,4-Dichlorophenylimino)methyl] N-ethyl S-(1-methylpropyl) N'-methyl phosphorodiamidothioate,

(44) N-[(4-Cyanophenylimino)methyl] N-ethyl N'-methyl S-(1-methylpropyl) phosphorodiamidothioate,

(45) N-Ethyl N'-methyl S-(1-methylpropyl) N-[(4-methylthiophenylimino)methyl] phosphorodiamidothioate,

(46) N-Ethyl N'-methyl N-[(4-methylcarbonylphenylimino) methyl] S-(1-methylpropyl) phosphorodiamidothioate,

(47) N-Ethyl N'-methyl N-[(3-methylphenylimino)-methyl] S-(1-methylpropyl) phosphorodiamidothioate,

(48) N-[(2-Chlorophenylimino)methyl] N-ethyl N'-methyl S-(1-methylpropyl) phosphorodiamidothioate,

(49) N-Ethyl N'-methyl N-[(4-methylphenylimino)-methyl] S-(1-methylpropyl) phosphorodiamidothioate,

(50) N-Ethyl N'-methyl S-(1-methylpropyl) N-[(4-phenoxyphenylimino)methyl] phosphorodiamidothioate,

(51) N'-Methyl S-(1-methylpropyl) N-(phenylimino)-methyl N-phenylmethyl phosphorodiamidothioate,

(52) N'-Methyl S-(1-methylpropyl) N-(2-methylthioethyl) N-(phenylimino)methyl phosphorodiamidothioate,

(53) N-(2-Methoxyethyl) N'-methyl S-(1-methylpropyl) N-(phenylimino)methyl phosphorodiamidothioate,

(54) N-(2-Ethoxycarbonylethyl) N'-methyl S-(1-methyl-propyl) N-(phenylimino)methyl phosphorodiamothioate,

EXAMPLE 55

N-Ethyl N'-methoxycarbonylmethyl S-(1-methylpropyl) N-(phenylimino)methyl phosphorodiamidothioate N-Ethyl N'-phenyl formamidine, 3.26 g. (0.02 mole) is added to a solution of S-(1-methylpropyl) phosphorodichloridothioate, 4.56 g. (0.02 mole), and triethylamine, 7.29 g. (0.07 mole), in 50 ml. of THF at 5° C. After stirring one hour, glycine methyl ester hydrochloride is added portionwise over 2 min. The reaction is stirred overnight at room temperature, filtered, and extracted with 50 ml. of sodium acetate/acetic acid buffer, pH 5, then water, dried over 4A molecular sieves, and concentrated to give 5.1 g. of product.

The following examples are prepared in an analogous manner.

(56) N'-(2-Ethoxycarbonyl)ethyl N-ethyl S-(1-methylpropyl) N-(phenylimino)methyl phosphorodiamidothioate,

(57) N-Ethyl N'-(3-methoxycarbonyl)propyl S-(1-methylpropyl)N-(phenylimino)methyl phosphorodiamidothioate,

(58) N-Ethyl N'-(4-methoxycarbonyl)butyl S-(1-methylpropyl)N-(phenylimino)methyl phosphorodiamidothioate,

(59) N-Ethyl N'-(2-ethylthioethyl) S-(1-methylpropyl) N-(phenylimino)methyl phosphorodiamidothioate,

EXAMPLE 60

N-Ethyl N'-(dimethylamino) S-(1-methylpropyl) N-(phenylimino)methyl phosphorodiamidothioate N-Ethyl N'-phenyl formamidine, 3.0 g (0.02 mole), is added portionwise to a solution of S-(1-methylpropyl) phosphorodichloridothioate, 4.18 g. (0.02 mole), and triethylamine, 4.45 g (0.044 mole), in 40 ml. of THF at 5°–10° C. The reaction is stirred 2 hrs. at room temperature, cooled to 5°–7° C. and N',N'-dimethylhydrazine, 1.30 g. (0.02 moles), is added. The reaction is stirred 2 days at room temperature, filtered, concentrated and the concentrate was then diluted with ether, extracted with water, dried over 4A molecular sieves, and evaporated to give 4.5 g. of product.

The following example is prepared in an analogous manner.

(61) N-Ethyl N'-(2-methoxyethyl) S-(1-methylpropyl) N-(phenylimino) methyl phosphorodiamidothioate

EXAMPLE 62

N-Ethyl S-(1-methylpropyl) N-(phenylimino)methyl phosphorodiamidothioate

N-Ethyl N'-phenyl formamidine, 8.89 g. (0.06 mole), is added portionwise over 15 min. to a solution of S-(1- methylpropyl) phosphorodichlorothioate, 12.4 g. (0.06 mole), and triethylamine, 13.4 g. (0.13 mole), in 250 ml. of ether at 5°–10° C. The reaction is stirred for one hour at room temperature, cooled to 4° C., and ammonia is bubbled in for three 5 min. periods employing a nitrogen bubbler metering gauge. The mixture is filtered, concentrated and dissolved in toluene. After washing with two 100 ml portions of sodium acetate/acetic acid buffer solution pH 5 and water, the toluene solution is dried over 4A molecular sieves and concentrated to give the product.

EXAMPLE 63

N-Methyl S,S-di(1-methylpropyl) N-(phenylimino)methyl phosphoramidothioate

A solution of N-methyl-N'-phenyl formamidine 3.0 g. (0.22 mole) and triethylamine, 2.26 g. (0.22 mole) in 15 ml. of THF is added dropwise to an ice-cooled solution of S-(1-methylpropyl) phosphorodichloridothioate, 4.41 g. (0.024 mole) in 50 ml. of THF. After 1 hour at room temperature, the mixture is cooled to 10° C. and a solution of (1-methylpropyl) thiol, 2.02 g. (0.024 mole), and triethylamine, 2.25 g. (0.022 mole) in 10 ml. of THF is added. The reaction is stirred 16 hours at room temperature, diluted with 100 ml. of ether, filtered, and evaporated to give an oil. This is diluted with ether/hexane (1:1) washed with water, dried over 4 A molecular sieves, and evaporated. Chromatography of the residual oil (elution with 10% ether in benzene) gives the product as an oil, 1.0 g.

(64) N-(2-Cyanoethyl) S,S'-di(1-methylpropyl) N-(phenylimino)methyl phosphoramidodithioate,

(65) N-Ethyl N-[(2-methylphenylimino)methyl] S,S',-di(1-methylpropyl) phosphoramidodithioate,

(66) N-Ethyl N-[(2-methylphenylimino)methyl] S-(1-methylpropyl) S'-propyl phosphoramidodithioate,

(67) N-Methyl N-[(4-methylphenylimino)methyl] S,S'-dipropyl phosphoramidodithioate,

(68) N-methyl N-[(4-methylphenylimino)methyl] S,S'-di(1-methylpropyl) phosphoramidodithioate,

(69) N-Methyl N-[(4-methylphenylimino)methyl] S-(1-methylpropyl) S'-propyl phosphorodiamidothioate,

EXAMPLE 70

N-Methyl S-(1-methylpropyl) O-phenyl N-(phenylimino)methyl phosphoramidothioate

A solution of S-(1-methylpropyl) O-phenyl phosphorochloridothioate, 7.0 g. (0.03 mole) in 30 ml. of THF was added dropwise to an ice-cooled solution of N-methyl-N'-phenyl formamidine, 4.24 g. (0.03 mole) and triethylamine, 5.25 g. (0.05 mole) in 80 ml. of THF. The reaction is stirred 20 hours at room temperature, filtered, and evaporated to give an oil which is chromatographed on Biosil A. Elution with 10% ether in toluene gives 4.86 g.

(71) N-Methyl O-phenyl N-(phenylimino)methyl S-propyl phosphoramidothioate,

(72) N-Methyl O-phenyl N-[1-(phenylimino)ethyl] S-propyl phosphoramidothioate,

(73) N-Ethyl O-phenyl N-(phenylimino)methyl S-(1-methylpropyl) phosphoramidothioate,

(74) N-[(4-Chlorophenylimino)methyl] N-methyl S-(1-methylpropyl) O-phenyl phosphoramidothioate,

(75) N-Methyl N-[(4-methylphenylimino)methyl] S-(1-methylpropyl) O-phenyl phosphoramidothioate,

(76) N-Methyl S-(2-methylpropyl) N-(phenylimino)methyl O-phenyl phosphoramidothioate,

(77) N-Ethyl O-phenyl N-(phenylimino)methyl S-propyl phosphoramidothioate,

(78) N-(2-Cyanoethyl) S-(1-methylpropyl) O-phenyl N-(phenylimino)methyl phosphoramidothioate,

(79) S-(1-Methylpropyl) O-phenyl N-(phenylimino)methyl N-(2-propenyl) phosphoramidothioate,

EXAMPLE 80

N-Methyl S-(1-methylpropyl) Q-(4-nitrophenyl) N-(phenylimino)methyl phosphoramidothioate A solution of N-methyl-N'-phenyl formamidine, 5.36 g. (0.04 mole), and triethylamine, 10.2 g. (0.1 mole), in 20 ml. of THF is added dropwise to an ice-cooled solution of S-(1-methylpropyl) phosphorodichloridothioate, 8.28 g. (0.04 mole) in 50 ml. of THF. After 2 hours at room temperature, a solution of 4-nitrophenol, 5.28 g. (0.04 mole), and triethylamine, 10.2 g. (0.1 mole) is added. The mixture is stirred 18 hours, filtered, and evaporated to give 17.9 g. of oil. Chromotography of 4 g. on Biosil A (toluene elution), gives 0.58 g.

The above examples of the compounds embraced by Formula I, and which are prepared in the manner previously described, are listed as Examples 1 to 80 in Table I.

TABLE I

| Example No. | R | $R^1$ | Y | Y' | $R^2$ | $R^3$ |
|---|---|---|---|---|---|---|
| 1 | H | $CH_3$ | 2-$CH_3$ | H | $NHCH_3$ | s-$C_4H_9$ |
| 2 | H | $CH_2CH=CH_2$ | H | H | $NHCH_3$ | s-$C_4H_9$ |
| 3 | H | $CH_2CH_2CN$ | 4-$CH_3$ | H | $NHCH_3$ | s-$C_4H_9$ |
| 4 | H | $CH_3$ | 2-$CH_3$ | H | $NHCH_3$ | n-$C_3H_7$ |
| 5 | H | $CH_3$ | 2-$CH_3$ | 4-Cl | $NHCH_3$ | s-$C_4H_9$ |
| 6 | H | $CH_3$ | H | H | $NHC_3H_7$-n | n-$C_3H_7$ |
| 7 | H | $CH_2CH=CH_2$ | 4-Cl | H | $NHC_3H_7$-n | n-$C_3H_7$ |
| 8 | H | $CH_3$ | H | H | $NHCH_3$ | s-$C_4H_9$ |
| 9 | H | $CH_2CH=CH_2$ | 4-$CH_3$ | H | $NHCH_3$ | s-$C_4H_9$ |
| 10 | H | $C_2H_5$ | 4-$CH_3$ | H | $NHC_3H_7$-n | s-$C_4H_9$ |
| 11 | H | $CH_3$ | 4-$CH_3$ | H | $NHC_3H_7$-i | n-$C_3H_7$ |
| 12 | H | $C_2H_5$ | 4-Cl | H | $NHC_3H_7$-i | s-$C_4H_9$ |
| 13 | H | $C_2H_5$ | 4-$CH_3$ | H | $NHCH_3$ | s-$C_4H_9$ |

TABLE I-continued

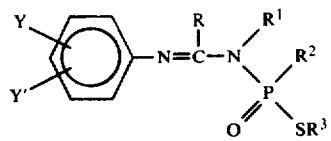

| Example No. | R | R¹ | Y | Y' | R² | R³ |
|---|---|---|---|---|---|---|
| 14 | H | $C_2H_5$ | 3-Cl | H | $NHCH_3$ | s-$C_4H_9$ |
| 15 | H | $CH_2CH_2CN$ | 2-$CH_3$ | H | $NHCH_3$ | s-$C_4H_9$ |
| 16 | $CH_3$ | $CH_3$ | H | H | $NHCH_3$ | s-$C_4H_9$ |
| 17 | H | $CH_2CH_2CN$ | H | H | $NHCH_3$ | s-$C_4H_9$ |
| 18 | H | n-$C_3H_7$ | 4-$CH_3$ | H | $NHCH_3$ | s-$C_4H_9$ |
| 19 | H | $CH_2CH=CH_2$ | 4-Cl | H | $NHCH_3$ | s-$C_4H_9$ |
| 20 | H | $C_2H_5$ | 4-$CH_3$ | H | $NHCH_2CH=CH_2$ | s-$C_4H_9$ |
| 21 | H | $CH_2CH=CH_2$ | 4-$CH_3$ | H | $NHC_3H_7$-n | n-$C_3H_7$ |
| 22 | H | $CH_3$ | H | H | $NHC_2H_5$ | s-$C_4H_9$ |
| 23 | H | $CH_3$ | H | H | $N(CH_3)_2$ | s-$C_4H_9$ |
| 24 | $CH_3$ | $CH_3$ | H | H | $N(CH_3)_2$ | s-$C_4H_9$ |
| 25 | $CH_3$ | $CH_3$ | H | H | $N(CH_3)_2$ | n-$C_3H_7$ |
| 26 | H | $C_2H_5$ | H | H | $NHC_2H_5$ | s-$C_4H_9$ |
| 27 | H | $C_2H_5$ | 4-$CH_3$ | H | $NHC_2H_5$ | s-$C_4H_9$ |
| 28 | H | $C_2H_5$ | H | H | $NHCH_3$ | n-$C_3H_7$ |
| 29 | H | $C_2H_5$ | H | H | $NHC_2H_5$ | n-$C_3H_7$ |
| 30 | H | $C_2H_5$ | H | H | $NHCH_3$ | s-$C_4H_9$ |
| 31 | H | $CH_3$ | H | H | $NHC_2H_5$ | n-$C_3H_7$ |
| 32 | H | $CH_3$ | H | H | $NHCH_3$ | n-$C_3H_7$ |
| 33 | H | $C_2H_5$ | 4-$CH_3$ | H | $N(CH_3)_2$ | s-$C_4H_9$ |
| 34 | H | $C_2H_5$ | 2-$CH_3$ | H | $NHCH_3$ | s-$C_4H_9$ |
| 35 | H | $C_2H_5$ | 2-$CH_3$ | H | $NHC_2H_5$ | s-$C_4H_9$ |
| 36 | H | $CH_2CH=CH_2$ | H | H | $NHCH_3$ | n-$C_3H_7$ |
| 37 | H | $C_2H_5$ | H | H | $NHCH_3$ | i-$C_4H_9$ |
| 38 | H | $CH_2CH=CH_2$ | H | H | $NHC_2H_5$ | s-$C_4H_9$ |
| 39 | H | $C_2H_5$ | 4-$OCH_3$ | H | $NHCH_3$ | s-$C_4H_9$ |
| 40 | H | $C_2H_5$ | 4-$OCH_3$ | H | $NHCH_3$ | i-$C_4H_9$ |
| 41 | H | $C_2H_5$ | 4-$CH_3$ | H | $NHCH_3$ | n-$C_3H_7$ |
| 42 | H | $C_2H_5$ | 2-Cl | 4-Cl | $NHCH_3$ | s-$C_4H_9$ |
| 43 | H | $C_2H_5$ | 3-Cl | 4-Cl | $NHCH_3$ | s-$C_4H_9$ |
| 44 | H | $C_2H_5$ | 4-CN | H | $NHCH_3$ | s-$C_4H_9$ |
| 45 | H | $C_2H_5$ | 4-$SCH_3$ | H | $NHCH_3$ | s-$C_4H_9$ |
| 46 | H | $C_2H_5$ | 4-$COCH_3$ | H | $NHCH_3$ | s-$C_4H_9$ |
| 47 | H | $C_2H_5$ | 4-$COCH_3$ | H | $NHCH_3$ | s-$C_3H_7$ |
| 48 | H | $C_2H_5$ | 2-Cl | H | $NHCH_3$ | s-$C_4H_9$ |
| 49 | H | $C_2H_5$ | 4-$CH_3$ | H | $NHCH_3$ | i-$C_4H_9$ |
| 50 | H | $C_2H_5$ | 4-$OC_6H_5$ | H | $NHCH_3$ | s-$C_4H_9$ |
| 51 | H | $C_2H_5$ | H | H | $NHCH_3$ | s-$C_4H_9$ |
| 52 | H | $CH_2CH_2SCH_3$ | H | H | $NHCH_3$ | s-$C_4H_9$ |
| 53 | H | $CH_2CH_2OCH_3$ | H | H | $NHCH_3$ | s-$C_3H_7$ |
| 54 | H | $CH_2CH_2CO_2C_2H_5$ | H | H | $NHCH_3$ | s-$C_4H_9$ |
| 55 | H | $CH_2CH_3$ | H | H | $NHCH_3$ | s-$C_4H_9$ |
| 56 | H | $CH_2CH_3$ | H | H | $NHCH_2CH_2CO_2C_2H_5$ | s-$C_4H_9$ |
| 57 | H | $CH_2CH_3$ | H | H | $NH(CH_2)_3CO_2CH_3$ | s-$C_4H_9$ |
| 58 | H | $CH_2CH_3$ | H | H | $NH(CH_2)_4CO_2CH_3$ | s-$C_4H_9$ |
| 59 | H | $CH_2CH_3$ | H | H | $NHCH_2CH_2SC_2H_5$ | s-$C_4H_9$ |
| 60 | H | $CH_2CH_3$ | H | H | $NHN(CH_3)_2$ | s-$C_4H_9$ |
| 61 | H | $CH_2CH_3$ | H | H | $NHCH_2CH_2OCH_3$ | s-$C_4H_9$ |
| 62 | H | $CH_2CH_3$ | H | H | $NH_2$ | s-$C_4H_9$ |
| 63 | H | $CH_3$ | H | H | $S-C_4H_9$-s | s-$C_4H_9$ |
| 64 | H | $CH_2CH_2CN$ | H | H | $S-C_4H_9$-s | s-$C_4H_9$ |
| 65 | H | $C_2H_5$ | 2-$CH_3$ | H | $S-C_4H_9$-s | s-$C_4H_9$ |
| 66 | H | $C_2H_5$ | 2-$CH_3$ | H | $S-C_3H_7$-n | s-$C_4H_9$ |
| 67 | H | $CH_3$ | 4-$CH_3$ | H | $S-C_3H_7$-n | s-$C_3H_7$ |
| 68 | H | $CH_3$ | 4-$CH_3$ | H | $S-C_4H_9$-s | s-$C_4H_9$ |
| 69 | H | $CH_3$ | 4-$CH_3$ | H | $S-C_3H_7$-n | s-$C_4H_9$ |
| 70 | H | $CH_3$ | H | H | $OC_6H_5$ | s-$C_4H_9$ |
| 71 | H | $CH_3$ | H | H | $OC_6H_5$ | n-$C_3H_7$ |
| 72 | $CH_3$ | $CH_3$ | H | H | $OC_6H_5$ | n-$C_3H_7$ |
| 73 | H | $C_2H_5$ | H | H | $OC_6H_5$ | s-$C_4H_9$ |
| 74 | H | $CH_3$ | 4-Cl | H | $OC_6H_5$ | s-$C_4H_9$ |
| 75 | H | $CH_3$ | 4-$CH_3$ | H | $OC_6H_5$ | s-$C_4H_9$ |
| 76 | H | $CH_3$ | H | H | $OC_6H_5$ | i-$C_4H_9$ |
| 77 | H | $C_2H_5$ | H | H | $OC_6H_5$ | n-$C_3H_7$ |
| 78 | H | $CH_2CH_2CN$ | H | H | $OC_6H_5$ | s-$C_4H_9$ |
| 79 | H | $CH_2CH=CH_2$ | H | H | $OC_6H_5$ | s-$C_4H_9$ |
| 80 | H | $CH_3$ | H | H | $OC_6H_4$-4-$NO_2$ | s-$C_4H_9$ |

TABLE II
ELEMENTAL ANALYSIS

| Example No. | Emp. Formula | Calculated (found) C | H | N |
|---|---|---|---|---|
| 1 | $C_{14}H_{24}N_3OPS$ | 53.7 (54.3) | 7.66 (8.00) | 13.4 (13.3) |
| 2 | $C_{15}H_{24}N_3OPS$ | 55.4 (55.0) | 7.38 (7.47) | 12.9 (12.4) |
| 3 | $C_{16}H_{25}N_4OPS$ | 54.5 (54.9) | 7.11 (7.30) | 15.9 (15.3) |
| 4 | $C_{13}H_{22}N_3OPS$ | 52.5 (53.8) | 7.58 (7.24) | 14.0 (12.8) |
| 5 | $C_{14}H_{23}ClN_3OPS$ | 48.3 (50.0) | 6.66 (6.53) | 12.1 (12.4) |
| 6 | $C_{14}H_{24}N_3OPS$ | 53.7 (51.1) | 7.72 (7.15) | 13.4 (12.3) |
| 7 | $C_{16}H_{25}ClN_3OPS$ | 51.4 (52.6) | 6.73 (6.21) | 11.2 (10.5) |
| 8 | $C_{13}H_{22}N_3OPS$ | 52.1 (52.4) | 7.34 (7.63) | 14.0 (14.0) |
| 9 | $C_{16}H_{26}N_3OPS$ | 56.7 (56.6) | 7.65 (7.74) | 12.4 (12.3) |
| 10 | $C_{17}H_{30}N_3OPS$ | 57.4 (58.0) | 8.51 (8.73) | 11.8 (11.6) |
| 11 | $C_{15}H_{26}N_3OPS$ | 55.0 (55.8) | 8.01 (8.24) | 12.8 (12.6) |
| 12 | $C_{16}H_{27}ClN_3OPS$ | 51.6 (51.5) | 7.16 (7.52) | 11.1 (11.4) |
| 13 | $C_{15}H_{26}N_3OPS$ | 55.0 (55.4) | 7.95 (8.31) | 12.8 (12.9) |
| 14 | $C_{14}H_{23}ClN_3OPS$ | 48.3 (48.3) | 6.62 (6.92) | 9.22 (11.8) |
| 15 | $C_{16}H_{25}N_4OPS$ | 54.5 (53.2) | 7.11 (7.30) | 15.9 (15.3) |
| 16 | $C_{14}H_{24}N_3OPS$ | 53.7 (51.7) | 7.67 (7.66) | 13.4 (12.7) |
| 17 | $C_{15}H_{23}N_4OPS$ | 53.3 (54.0) | 6.80 (6.99) | 16.6 (15.8) |
| 18 | $C_{16}H_{28}N_3OPS$ | 56.3 (57.2) | 8.26 (8.19) | 12.3 (12.0) |
| 19 | $C_{15}H_{23}ClN_3OPS$ | 50.1 (50.1) | 6.44 (6.11) | 11.7 (11.4) |
| 20 | $C_{17}H_{28}N_3OPS$ | 57.5 (56.3) | 7.98 (8.18) | 12.0 (11.9) |
| 21 | $C_{17}H_{28}N_3OPS$ | 57.8 (57.3) | 7.98 (8.10) | 11.9 (12.0) |
| 22 | $C_{14}H_{24}N_3OPS$ | 53.2 (53.7) | 7.67 (7.77) | 13.4 (13.4) |
| 23 | $C_{14}H_{24}N_3OPS$ | 53.7 (52.3) | 7.72 (7.87) | 13.4 (13.6) |
| 24 | $C_{15}H_{26}N_2OPS$ | 57.5 (59.2) | 8.36 (8.18) | 8.94 (13.0) |
| 25 | $C_{14}H_{24}N_3OPS$ | 53.7 (54.2) | 7.72 (7.97) | 13.4 (13.6) |
| 26 | $C_{15}H_{26}N_3OPS$ | 55.0 (54.4) | 7.95 (8.17) | 12.8 (13.0) |
| 27 | $C_{16}H_{28}N_3OPS$ | 56.3 (55.6) | 8.21 (3.62) | 12.3 (12.6) |
| 28 | $C_{13}H_{22}N_3OPS$ | 55.9 (52.8) | 7.87 (7.50) | 15.1 (13.6) |
| 29 | $C_{14}H_{24}N_3OPS$ | 53.6 (53.1) | 7.66 (7.96) | 13.4 (13.2) |
| 30 | $C_{14}H_{24}N_3OPS$ | 53.6 (53.4) | 7.66 (7.37) | 13.4 (12.9) |
| 31 | $C_{13}H_{22}N_3OPS$ | 52.2 (52.3) | 7.35 (7.52) | 14.0 (13.9) |
| 32 | $C_{12}H_{20}N_3OPS$ | 50.5 (51.4) | 7.01 (7.22) | 14.7 (14.6) |
| 33 | $C_{16}H_{28}N_3OPS$ | 56.3 (55.2) | 8.26 (8.14) | 12.3 (12.7) |
| 34 | $C_{15}H_{26}N_3OPS$ | 55.0 (54.9) | 7.95 (8.07) | 12.8 (12.9) |
| 35 | $C_{16}H_{28}N_3OPS$ | 56.3 (56.6) | 8.21 (8.56) | 12.3 (12.4) |
| 36 | $C_{14}H_{22}N_3OPS$ | 54.0 (55.6) | 7.07 (7.39) | 13.5 (13.2) |
| 37 | IN TEST | | | |
| 38 | $C_{16}H_{24}N_3OPS$ | 56.7 (56.8) | 7.66 (7.76) | 12.4 (12.2) |
| 39 | $C_{15}H_{26}N_3OPS$ | 55.0 (51.4) | 8.01 (7.65) | 12.8 (11.6) |
| 40 | $C_{16}H_{26}N_3OPS$ | 55.0 (54.9) | 8.01 (7.35) | 12.8 (11.3) |
| 41 | $C_{14}H_{24}N_3OPS$ | 53.7 (53.7) | 7.67 (7.77) | 13.4 (12.9) |
| 42 | $C_{14}H_{22}ClN_3OPS$ | 44.0 (44.0) | 5.80 (5.74) | 11.0 (10.4) |
| 43 | $C_{14}H_{22}Cl_2N_3OPS$ | 44.0 (40.8) | 5.80 (5.19) | 11.0 (9.85) |
| 44 | $C_{15}H_{23}N_4OPS$ | 54.9 (52.7) | 7.01 (6.87) | 17.1 (15.3) |
| 45 | $C_{15}H_{26}N_3OPS_2$ | 50.0 (48.8) | 7.24 (7.67) | 11.7 (11.6) |
| 46 | $C_{16}H_{26}N_3O_2PS$ | 54.8 (49.5) | 7.32 (6.69) | 11.8 (10.2) |
| 47 | $C_{15}H_{26}N_3OPS$ | 55.0 (56.8) | 8.01 (7.93) | 12.8 (12.9) |
| 48 | $C_{14}H_{23}ClN_3OPS$ | 48.3 (48.4) | 5.66 (6.75) | 12.1 (11.9) |
| 49 | $C_{15}H_{26}N_3OPS$ | 55.0 (56.1) | 8.01 (7.92) | 12.8 (12.8) |
| 50 | $C_{19}H_{26}N_3OPS$ | 58.3 (58.5) | 6.70 (7.02) | 10.7 (10.8) |
| 51 | $C_{17}H_{26}N_3OPS$ | 58.1 (61.8) | 7.40 (7.37) | 12.0 (11.4) |
| 52 | $C_{15}H_{26}N_3OPS_2$ | 50.0 (50.8) | 7.24 (7.40) | 11.7 (11.3) |
| 53 | $C_{15}H_{26}N_3O_2PS$ | 52.3 (51.9) | 7.58 (7.82) | 12.2 (11.5) |
| 54 | $C_{20}H_{24}N_3O_2PS$ | 59.8 (60.4) | 6.02 (6.1) | 10.5 (10.8) |
| 55 | $C_{16}H_{26}N_3O_3PS$ | 51.7 (51.7) | 7.00 (7.41) | 11.3 (11.5) |
| 56 | $C_{17}H_{30}N_3O_3PS$ | 52.6 (53.1) | 7.80 (7.77) | 10.8 (10.6) |
| 57 | $C_{19}H_{32}N_3O_3PS$ | 55.1 (54.2) | 7.80 (8.13) | 10.1 (10.3) |
| 58 | $C_{19}H_{30}N_3O_3PS$ | 54.1 (52.1) | 7.50 (7.57) | 10.5 (10.2) |
| 59 | $C_{17}H_{30}N_3OPS_2$ | 52.6 (51.0) | 7.80 (7.80) | 10.8 (11.1) |
| 60 | $C_{15}H_{27}N_4OPS$ | 52.6 (52.4) | 7.90 (7.89) | 16.3 (16.2) |
| 61 | $C_{16}H_{28}N_3O_2PS$ | 53.8 (50.3) | 7.90 (8.06) | 11.7 (11.3) |
| 62 | $C_{13}H_{22}N_3OPS$ | 52.1 (49.0) | 7.40 (7.88) | 14.0 (13.3) |
| 63 | $C_{16}H_{27}N_2OPS_2$ | 53.6 (52.3) | 7.59 (7.86) | 7.82 (7.93) |
| 64 | $C_{18}H_{28}N_3OPS_2$ | 54.4 (51.9) | 7.71 (7.61) | 10.6 (9.61) |
| 65 | $C_{18}H_{31}N_2OPS_2$ | 55.9 (54.5) | 8.08 (8.42) | 7.25 (7.60) |
| 66 | $C_{17}H_{29}N_2OPS_2$ | 54.8 (54.6) | 7.85 (8.06) | 7.52 (8.40) |
| 67 | $C_{15}H_{25}N_2OPS_2$ | 52.3 (52.0) | 7.31 (7.75) | 8.13 (7.92) |
| 68 | $C_{17}H_{29}N_2OPS_2$ | 54.8 (54.4) | 7.85 (8.05) | 7.52 (8.09) |
| 69 | $C_{16}H_{27}N_2OPS_2$ | 53.6 (53.1) | 7.59 (7.98) | 7.82 (7.73) |
| 70 | $C_{18}H_{23}N_2O_2PS$ | 59.7 (57.9) | 6.39 (6.12) | 7.73 (8.03) |
| 71 | $C_{17}H_{21}N_2O_2PS$ | 58.6 (56.4) | 6.07 (5.76) | 8.04 (7.29) |
| 72 | $C_{18}H_{23}N_2O_2PS$ | 59.7 (57.9) | 6.40 (6.10) | 7.73 (6.37) |
| 73 | $C_{19}H_{25}N_2O_2PS$ | 60.6 (61.1) | 6.69 (6.82) | 7.44 (7.55) |
| 74 | $C_{17}H_{22}ClN_2O_2PS$ | 53.1 (55.2) | 5.76 (5.72) | 7.28 (7.14) |
| 75 | $C_{19}H_{25}N_2O_2PS$ | 60.6 (60.3) | 6.69 (6.66) | 7.44 (7.09) |
| 76 | $C_{18}H_{23}N_2OPS$ | 59.7 (60.2) | 6.40 (6.40) | 7.73 (7.75) |
| 77 | $C_{18}H_{23}N_2OPS$ | 59.7 (60.0) | 6.40 (6.41) | 7.73 (7.01) |
| 78 | $C_{20}H_{24}N_3OPS$ | 59.8 (60.4) | 6.02 (6.17) | 10.5 (10.8) |
| 79 | $C_{20}H_{25}N_2O_2PS$ | 61.8 (62.4) | 6.48 (6.68) | 7.21 (11.4) |
| 80 | $C_{18}H_{22}N_3O_4PS$ | 53.3 (51.5) | 5.44 (5.56) | 10.3 (9.07) |

Initial evaluations are made on the following mite, insects, and nematode:

| Code Symbol | Common Name | Latin Name |
|---|---|---|
| TSM | Two-spotted spider mite | *Tetranychus urticae* |
| GPA | Green peach aphis | *Myzus persicae* |
| MBB | Mexican bean beetle | *Epilachna varivestis* |
| SAW | Southern armyworm | *Spodoptera eridania* |
| CRW | Southern corn rootworm, ova and larvae | *Diabrotica undecimpunctata howardi* |
| nema | Southern root-knot nematode | *Meloidogyne incognita* |
| HF | House Fly | *Musca domestica* |
| RB | Rice Blast | *Piricularia oryzae* |

A test solution containing 600 ppm of test compound can be made by dissolving the test compound in a solvent (acetone:methanol, 1:1), adding surfactant and then water to give an acetone:methanol:water system of 10:10:80. A 1:1 mixture of an alkylarylpolyetheralcohol (commercially available under the trademark Triton X-155) and a modified phthalic glycerol alkyl resin (commercially available under the trademark Triton B-1956) can be utilized at the equivalent to one ounce per 100 gallons of test solution and a surfactant.

For the mite test, infested bean (*Phaseolus limeanus*) leaf discs (1.25 inches in diameter) containing about 50 mites and for green peach aphid tests, infested brocoli (*Brassica oleracea italica*) leaves or portions thereof containing about 50 aphids are placed in a Petri dish lid on a moistened piece of cotton. The leaves are then sprayed with the test solution using a rotating turntable. They are held for 24 hours and then the percent kill is determined.

For the bean beetle and armyworm test, detached bean leaves on pieces of moistened filter paper are sprayed as above for the mite test in similar dishes and allowed to dry. One such dish is infested with 10 third instar Mexican bean beetle larvae, while another is infested with 10 third instar southern arymworm larvae. The dishes are covered. After holding for 48 hours, the percent kill is obtained.

For the house fly tests, half pint glass canning jars with a screened top are used. Food is supplied for the adult house flies. The jars containing the insects are sprayed using the turntable. In the house fly test, a percent knockdown is determined one hour after application, the percent kill after 24 hours.

For the nematode test, soil is homogeneously inoculated with a macerated blend of tomato roots heavily knitted with the root knot nematode. Ten milliliters of the test solution are added to 200 milliliters of the inoculated soil in a 16 oz. jar to give a concentration by volume of about 30 ppm. The jar is then shaken to insure thorough mixing, immediately uncapped, and allowed to air for 24 hours. The coil is then placed into a 3 inch plastic pot after which time 3 cucumber (*Cucumis sativus*) seeds are planted. About 23 days thereafter, the cucumber plants are removed from the soil and the root system examined for the presence of knits. A total of 25 knots or less is considered as a measure of control.

Ovicidal and larvicidal tests are conducted on representative compounds of this invention. These compounds demonstrate ovicidal and larvicidal activity.

For tests involving the southern corn rootworm (*Diabrotica undecimpunctata howardi*) ova and larvae, two layers of 4.25 cm. filter papers are placed in small, Petri dishes, and sprayed on the turntable with a 600 ppm solution of the test compound and air dried. About 100 eggs in about one milliliter of water are pipetted onto the filter paper and the dishes covered. These are held for 6 days and examined under the microscope. The percent kill values for ova and larvae are determined.

Fungicidal evaluation of compounds of this invention is carried out by way of a foliar screening test. The general procedure for the fungicidal test is to take potted plants in proper condition of growth for susceptibility to the plant diseases to be evaluated, to spray these on a moving belt and allow them to dry. The plants are then inoculated with the respective fungal spores and allowed to incubate until the disease symptoms and the disease control are read or estimated. Percentage of disease control is recorded.

Compounds of the present invention are tested at a concentration of 300 ppm in a solution or suspension made by dissolving a weighed amount of the candidate fungicide in a 50:50 mixture of acetone and methanol and then adding an equal volume of water.

Table III gives the results of the foregoing biological evaluations.

TABLE III

Screening Results, % Control[a]

| Example # | TSM[b] | GPA[b] | MBB[b] | SAW[b] | CRW E/L[c] | NEMA[d] |
|---|---|---|---|---|---|---|
| 1 | 100 | 100 | 100 | 100 | 67/100 | A |
| 2 | 100 | 100 | 100 | 100 | 34/150 | A |
| 3 | 100 | 100 | 100 | 100 | 0/85 | A |
| 4 | 100 | 67[c] | 30 | 100 | —/— | A |
| 5 | 100 | 100 | 100 | 100 | —/— | A |
| 6 | 0 | 0 | 20 | 40 | 0/0 | A |
| 7 | 100 | 100 | 100 | 10 | 0/100 | A |
| 8 | 100 | 100 | 100 | 100 | 71/100 | A |
| 9 | 100 | 100 | 100 | 100 | 36/88 | A |
| 10 | 67 | 100 | 90 | 10 | 0/86 | A |
| 11 | 100 | 100 | 20 | 0 | 0/81 | A |
| 12 | 0 | 0 | 100 | 10 | 0/100 | A |
| 13 | 100 | 100 | 90 | 100 | 91/100 | A |
| 14 | 100 | 100 | 100 | 100 | 63/100 | A |
| 15 | 100 | 100 | 100 | 100 | 0/98 | A |
| 16 | 100 | 100 | 100 | 100 | 0/0 | A |
| 17 | 100 | 94 | 90 | 100 | 0/98 | A |
| 18 | 100 | 100 | 100 | 100 | 45/100 | A |
| 19 | 100 | 100 | 100 | 100 | 51/100 | A |
| 20 | 100 | 100 | 80 | 0 | 0/98 | A |
| 21 | 0 | 0 | 20 | 40 | 0/0 | A |
| 22 | 100 | 100 | 100 | 100 | 0/100 | A |
| 23 | 100 | 100 | 100 | 100 | 0/100 | A |
| 24 | 100 | 100 | 100 | 0 | 0/97 | C |
| 25 | 100 | 100 | 20 | 0 | 0/94 | C |
| 26 | 100 | 100 | 100 | 100 | 53/100 | A |
| 27 | 100 | 100 | 100 | 100 | 55/100 | A |
| 28 | 100 | 100 | 20 | 100 | 59/100 | A |
| 29 | 100 | 83[c] | 80 | 100 | 46/84 | A |
| 30 | 100 | 100 | 100 | 100 | 100/— | A |
| 31 | 100 | 100 | 0 | 100 | 32/84 | A |
| 32 | 100 | 100 | 20 | 100 | 55/100 | A |
| 33 | 100 | 100 | 100 | 100 | 0/83 | A |
| 34 | 100 | 100 | 100 | 100 | 89/100 | A |

TABLE III-continued

Screening Results, % Control[a]

| Example # | TSM[b] | GPA[b] | MBB[b] | SAW[b] | CRW E/L[c] | NEMA[d] |
|---|---|---|---|---|---|---|
| 35 | 100 | 100 | 100 | 100 | 74/100 | A |
| 36 | 100 | 100 | 80 | 100 | 64/95 | A |
| 37 | 100 | 100 | 100 | 100 | 76/100 | A |
| 38 | 100 | 100 | 100 | 100 | 77/100 | A |
| 39 | 100 | 100 | 100 | 100 | 61/100 | A |
| 40 | 100 | 100 | 100 | 100 | 67/100 | A |
| 41 | 100 | 100 | 0 | 100 | 0/100 | A |
| 42 | 100 | 100 | 100 | 100 | 63/100 | A |
| 43 | 100 | 100 | 100 | 100 | 76/100 | A |
| 44 | 100 | 100 | 100 | 100 | 65/100 | A |
| 45 | 100 | 100 | 100 | 100 | 64/100 | A |
| 46 | 100 | 100 | 100 | 100 | 58/40 | A |
| 47 | 100 | 100 | 100 | 100 | 63/100 | A |
| 48 | 100 | 100 | 100 | 100 | 61/100 | A |
| 49 | 100 | 100 | 100 | 100 | 0/100 | A |
| 50 | 100 | 100 | 100 | 100 | 47/100 | A |
| 51 | 100 | 100 | 100 | 100 | 62/100 | A |
| 52 | 100 | 100 | 100 | 100 | 0/0 | A |
| 53 | 100 | 100 | 100 | 100 | 52/96 | A |
| 54 | 100 | 100 | 100 | 100 | 0/100 | A |
| 55 | 100 | 100 | 0 | 0 | 0/0 | A |
| 56 | 100 | 100 | 0 | 0 | 0/79 | A |
| 57 | 100 | 100 | 80 | 100 | 70/50 | A |
| 58 | 100 | 100 | 70 | 100 | 48/0 | A |
| 59 | 100 | 77[c] | 0 | 0 | 0/96 | A |
| 60 | 100 | 100 | 100 | 10 | 0/100 | A |
| 61 | 100 | 94 | 100 | 0 | 65/53 | A |
| 62 | 100 | 100 | 100 | 100 | 0/100 | A |
| 63 | 100 | 100 | 100 | 100 | 65/100 | A |
| 64 | 100 | 100 | 100 | 100 | 81/100 | A |
| 65 | 100 | 100 | 100 | 100 | 51/100 | A |
| 66 | 100 | 100 | 100 | 100 | 84/100 | A |
| 67 | 100 | 100 | 100 | 100 | 100/— | A |
| 68 | 100 | 100 | 100 | 100 | 92/100 | A[e] |
| 69 | 100 | 100 | 100 | 100 | 94/100 | A |
| 70 | 100 | 100 | 100 | 100 | 48/100 | A |
| 71 | 100 | 100 | 100 | 100 | 45/100 | A |
| 72 | 100 | 100 | 100 | 100 | 74/100 | A |
| 73 | 100 | 100 | 100 | 0 | 41/100 | A |
| 74 | 100 | 100 | 100 | 100 | 67/100 | A |
| 75 | 100 | 100 | 100 | 100 | 65/100 | A |
| 76 | 100 | 100 | 100 | 100 | 68/100 | A |
| 77 | 100 | 100 | 0 | 0 | 54/100 | A |
| 78 | 90 | 85 | 0 | 0 | 50/100 | A |
| 79 | 100 | 93 | 90 | 0 | 0/100 | A |
| 80 | 100 | 100 | 100 | 100 | 0/1 | A |

[a]TSM = two-spotted mite; GPA = green peach aphid; MBB = Mexican bean beetle; SAW = southern armyworm; CRW E/L = corn rootworm ova/larvae; nema = nematode.
[b]Insecticidal screening results; % control at 600 ppm
[c]Insecticidal screening results, % control at 150 ppm
[d]A = 0–9 knots on root; B = 10–25 knots on root; C = 25 knots on root (at 30 ppm in soil)
[e]A = 0–9 knots on root at 15 ppm in soil.

The compounds of the invention are useful for the protection of plants and animals, including mammals, from the ravages of harmful and annoying pests. These compounds are particularly effective against arthropods (in varying stages of development) and are especially effective against members of the Class Arachnoidea, which includes the Order Acarina, as represented by mites and ticks, and the Class Insecta, the insects. Among the arthropods which are effectively controlled by the compounds of the present invention are the chewing insects, e.g., the southern armyworm (*Spodoptera eridania*), the sucking insects, e.g., the green peach aphid (*Myzus persicae*), soil-dwelling insects, e.g., the southern corn rootworm (*Diabrotica undecimpunctata howardi*), mites, e.g., the two-spotted spider mite (*Tetranychus urticae*) and others.

The compounds of this invention are also active as fungicides. One of the plant fungus diseases controlled by compounds of this invention includes, for example, rice blast (*Piricularia Oryzae*). Example 4 gives 97 to 100% control of rice blast at 300 ppm.

Furthermore, compounds of this invention, particularly, compounds wherein R in Formula I is a hydrogen atom, possess nematocidal activity. Among the nematodes which are effectively controlled by the compounds of the present invention are soil nematodes, typified by the southern root knot nematode (*Meloidogyne incognita*).

Generally, control of pests is achieved in accordance with this invention by application of the compounds in pesticidally effective amounts (e.g., arthropodicidally effective amounts) either directly to the pests to be controlled or to the loci to be freed of or protected from attack by such pests. Plant protection loci may be defined as the aerial and subterranean portions of plants or propagative subunits and their immediate or future environs. For example, food, fiber, forage, forest, and ornamental crops and stored products thereof represent plant protection loci. Treatment with compounds of this invention of domestic animals, and their immediate environs similarly constitute representative loci for protection against various annoying ectoparasitic or endoparasitic Acarina (Acari) and Insecta. Many of the below formulations can be utilized on animals in the control of parasites. Thus, the compounds can be deposited on or in the soil, plants, insects, manmade structures, or other substrates as deposits, coatings, etc. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, inhibition, reduction in number of any combination thereof.

The term "pest" as employed in the specification and claims of this application refers to fungi, nematodes and various arthropods especially insects and acarids.

The phosphoramidates of this invention possess general utility as arthropodicides, particularly as against members of the class Arachnoidea, which includes the order Acarina, as represented by mites and ticks, and Insecta, the insects. Certain compounds of this invention are also active as nematocides and fungicides, particularly fungicides.

For use as pesticides, the compounds of this invention can be used as solutions in organic solvents or formulations. For example, they can be formulated as wettable powders, emulsifiable concentrates, dusts, granular formulations or flowable emulsifiable concentrates. In such formulations, the phosphoramidates are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual".

The phosphoramidates can be taken up or mixed with a finely particled solid carrier, as for example, clays, inorganic silicates, carbonates, and silicas. Organic carriers can also be employed. Dust concentrates are commonly made wherein phosphoramidates are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The phosphoramidates are usually present in the range of about 10 to about 35% by weight and surfactants from about 0.5 to about 10% by weight.

One convenient method for preparing a solid formulation is to impregnate the phosphoramidate onto the solid carrier by means of a volatile solvent such as acetone. In this manner, adjuvants, such as activators, adhesives, plant nutrients, synergists and various surfactants can also be incorporated.

Emulsifiable concentrate formulations can be prepared by dissolving the phosphoramidates of this invention in an agronomically acceptable organic solvent and adding a solvent-soluble emulsifying agent. Suitable solvents are usually water-immiscible and can be found in the hydrocarbon, ketone, ester, alcohol and amide groups of organic solvents. Mixtures of solvents are commonly employed. The surfactants useful as emulsifying agents can constitute about 0.5 to about 10% by weight of emulsifiable concentrate and can be anionic, cationic or non-ionic in character. The concentration of the active ingredients can vary from about 20 to about 50%.

For use as pesticidal agents, these compounds should be applied in an effective amount sufficient to exert the desired pesticidal activity by techniques well known in the art. Usually, this will involve the application of the phosphoramidate to the loci to be protected from or freed of pests in an effective amount when incorporated in an agronomically acceptable carrier. However, in certain situations, it may be desirable and advantageous to apply the compounds directly onto the loci to be protected from or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purpose for such application, the phosphoramidate being utilized, the frequency of dissemination and the like.

By "agronomically acceptable carrier" is meant any substance which can be utilized to dissolve, disperse, or diffuse the chemical incorporated therein without impairing the effectiveness of the toxic agent and which does no permanent damage to such environment as soil, equipment and agronomic crops.

For use as insecticides and acaricides, dilute sprays can be applied at concentrations of about 0.01 to about 20 pounds of the phosphoramidate ingredient per 100 gallons of spray. They are usually applied at about 0.1 to about 5 pounds per 100 gallons. In more concentrated sprays, the active ingredient is increased by a factor of about 2 to about 12. With dilute sprays, applications are usually made to the plants until run off is achieved, whereas with more concentrated low-volume sprays, the materials are applied as mists.

For use as a fungicide, the compounds of this invention can be applied as fungicidal sprays by methods commonly employed, such as, conventional high-gallonage hydraulic sprays, low-gallonage sprays, air-blast sprays, aerial sprays and dusts. The dilution and rate of application will depend upon the type of equipment employed, the method of application and diseases to be controlled, but the preferred effective amount is usually about 0.1 lb. to about 50 lbs. per acre of the active ingredient.

As a fungicidal seed protectant, the amount of toxicant coated on the seed is usually at a dosage rate of about 0.1 to about 20 ounces per hundred pounds of seed. As a soil fungicide the chemical can be incorporated in the soil or applied to the surface usually at a rate of about 0.1 to about 50 lbs. per acre. As a foliar fungicide, the toxicant is usually applied to growing plants at a rate of about 0.25 to about 10 lbs. per acre.

For use as a nematocide, systemic agent, or as a soil insecticide, the phosphoramidates can be applied as a solid formulation, preferably a granular formulation or as a diluted liquid preparation, by broadcasting, side-dressing soil incorporation or seed treatment.

The composition can also be added to transplant or irrigation water or to units employed in propagation, such as seeds, tubers, roots, seedlings, etc., so as to disinfect and/or provide residual protection from nematodes, soil insects (and mites) and via systemic untake, foliar pests. The application rate can be from about 0.5 to about 50 pounds per acre; however, higher rates can also be used. The preferred rate is from about 1 to about 25 pounds per acre. For soil incorporation, the compounds of this invention can be mixed with the soil or other growth medium at a rate of about 1 to about 100 ppm of active ingredient.

The compounds of this invention can be utilized as the sole pesticidal agents or they can be employed in conjunction with other bactericides, fungicides, herbicides, insecticides, acaricides, nematocides and comparable pesticides.

Many variations of this invention are possible without departing from the spirit or scope thereof.

We claim:

1. A compound of the formula:

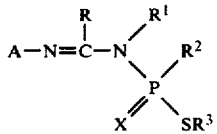

wherein

A is an unsubstituted ($C_6-C_{10}$) aryl group; or a ($C_6-C_{10}$) aryl group substituted with up to three substituents selected from the group consisting of cyano, nitro, halogen, ($C_1-C_6$) alkyl, ($C_1-C_6$) alkoxy, ($C_1-C_6$) alkylthio, acetoxy, trifluoromethyl, ($C_1-C_6$) alkylaminocarbonyl, di-($C_1-C_6$) alkylaminocarbonyl, halo ($C_1-C_6$) alkyl, ($C_1-C_6$) alkylsulfinyl, ($C_1-C_6$) alkylsulfonyl, $C_6-C_{10}$) aryloxy, ($C_6-C_{10}$) arylthio, arylsulfinyl, arylsulfonyl or ($C_1-C_6$) alkylcarbonyl;

R is a hydrogen atom or an unsubstituted ($C_1-C_6$) alkyl group;

$R^1$ is (a) an unsubstituted ($C_1-C_6$) alkyl group, or a ($C_1-C_6$) alkyl group substituted with one substituent selected from the group consisting of cyano, furyl, ($C_1-C_6$) alkoxy, ($C_1-C_6$) alkylthio, ($C_1-C_6$) alkylsulfinyl, ($C_1-C_6$) alkylsulfonyl, ($C_3-C_6$) alkenyloxy, ($C_3-C_6$)alkenyloxycarbonyl, ($C_1-C_6$) alkylcarbonyl, ($C_1-C_6$) alkoxycarbonyl, ($C_1-C_6$)-alkylcarbonyloxy, mono- or di-($C_1-C_6$) alkylaminocarbonyl, di-($C_1-C_6$) alkylamino, ($C_6-C_{10}$) aryloxy, ($C_6-C_{10}$) arylthio, ($C_6-C_{10}$) arylsulfinyl, ($C_6-C_{10}$) arylsulfonyl, ($C_6-C_{10}$) arylcarbonyl, ($C_6-C_{10}$) aryloxycarbonyl, ($C_6-C_{10}$) arylaminocarbonyl;

(b) an unsubstituted ($C_3-C_8$) cycloalkyl group;

(c) an unsubstituted ($C_3-C_6$) alkenyl group or a ($C_3-C_6$) alkenyl group with up to two substituents selected from the group consisting of cyano, halogen, ($C_1-C_6$) alkoxycarbonyl, and an unsubstituted ($C_6-C_{10}$) aryl group or a ($C_6-C_{10}$) aryl group substituted with up to three substituents selected from the group consisting of cyano, nitro, halogen, ($C_1-C_6$) alkyl, ($C_1-C_6$) alkoxy, ($C_1-C_6$) alkylthio, ($C_1-C_6$) alkylaminocarbonyl, di-($C_1-C_6$) alkylaminocarbonyl, and halo ($C_1-C_6$) alkyl;

(d) an unsubstituted ($C_3-C_6$) alkynyl group;

(e) an unsubstituted aralkyl group of up to 11 carbon atoms, or an aralkyl group of up to 11 carbon atoms the aryl portion of which is substituted with up to three substituents selected from the group consisting of cyano, nitro, halogen, ($C_1-C_6$) alkyl, ($C_1-C_6$) alkoxy, ($C_1-C_6$) alkylthio, ($C_1-C_6$) alkylaminocarbonyl, di-($C_1-C_6$) alkylaminocarbonyl and halo ($C_1-C_6$) alkyl;

$R^2$ is (a) ($C_1-C_6$) alkylthio;

(b) ($C_6-C_{10}$) aryloxy; or (c) a group of the formula NZ'Z" wherein Z' is hydrogen, ($C_1-C_6$) alkyl, Z" is hydrogen or ($C_1-C_6$) alkyl; or ($C_3-C_6$) alkenyl, di($C_1-C_3$)alkyl amino, 2-ethylthioethyl 2-methoxyethyl or ($C_1-C_4$) alkoxycarbonylalkyl ($C_1-C_4$);

$R^3$ is unsubstituted ($C_1-C_6$) alkyl; and

X is oxygen or sulfur.

2. A compound according to claim 1 wherein A has the formula

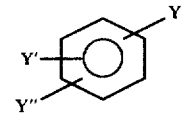

wherein Y, Y' and Y" are independently hydrogen, cyano, nitro, halogen, ($C_1-C_4$) alkyl, ($C_1-C_4$) alkoxy, ($C_1-C_4$) alkylthio, acetyl, trifluoromethyl, ($C_1-C_4$) alkylsulfinyl, ($C_1-C_4$) alkylsulfonyl and phenyloxy.

3. A compound according to claim 2 wherein R is hydrogen or unsubstituted ($C_1-C_4$) alkyl;

$R^1$ is (a) an unsubstituted ($C_1-C_4$) alkyl group, or a ($C_1-C_4$) alkyl group substituted with one substituent selected from the group consisting of cyano, ($C_1-C_4$) alkoxy, ($C_1-C_4$) alkylthio, ($C_1-C_4$) alkylsulfinyl, ($C_1-C_4$) alkylsulfonyl, ($C_1-C_4$) alkylcarbonyl, ($C_1-C_4$) alkoxycarbonyl, ($C_1-C_4$) alkylcarbonyloxy, mono or di-($C_1-C_4$) alkylaminocarbonyl, di-($C_1-C_4$) alkylamino, ($C_3-C_4$) alkenyloxy, ($C_3-C_4$) alkenyloxycarbonyl, phenyloxy, phenylthio, phenylsulfinyl, phenylsulfonyl, phenycarbonyl, phenyloxycarbonyl, phenylcarbonyloxy, and phenylaminocarbonyl;

(b) an unsubstituted (C₃-C₆) cycloalkyl group;
(c) an unsubstituted (C₃-C₄) alkenyl group or a (C₃-C₄) alkenyl group substituted with up to two substituents selected from the group consisting of cyano, halogen, (C₁-C₃) alkoxycarbonyl, and an unsubstituted phenyl;
(d) an unsubstituted (C₃-C₄) alkynyl;
(e) an unsubstituted benzyl or phenethyl group or a benzyl or phenethyl group substituted with up to three substituents selected from the group consisting of cyano, nitro, halogen, (C₁-C₄) alkyl, (C₁-C₄) alkoxy, (C₁-C₄) alkylthio, (C₁-C₄) alkylaminocarbonyl, di-(C₁-C₄) alkylaminocarbonyl and halo (C₁-C₆) alkyl;

$R^3$ is an unsubstituted (C₁-C₄) alkyl group; and
X is oxygen.

4. A compound according to claim 3 wherein R is hydrogen.

5. A compound according to claim 4 wherein Y, Y' and Y" are independently hydrogen, cyano, chloro, fluoro, bromo, methyl, ethyl, methylthio, acetyl trifluoromethyl, methylsulfinyl, methylsulfonyl, phenoxy and methoxy.

6. A compound according to claim 5 wherein $R^2$ is a group of the formula NZ'Z" wherein Z' is hydrogen; Z" is methyl or ethyl; and $R^3$ is (C₃-C₄) alkyl.

7. A compound according to claim 6 wherein Y, Y' and Y" are independently hydrogen, methyl, chloro, cyano, methylthio, phenoxy, acetyl.

8. A compound according to claim 7 wherein $R^2$ is phenyoxy.

9. A compound according to claim 7 wherein $R^2$ is (C₁-C₄) alkylthio.

10. A compound according to claim 7 wherein $R^2$ is (C₃-C₄) alkylthio.

11. A compound according to claim 3 having the following formula

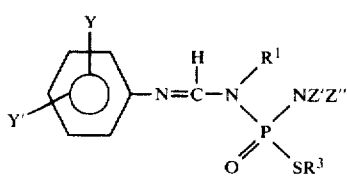

wherein
$R^1$ is a methyl group, an ethyl group, an unsubstituted (C₅-C₇) cycloalkyl group, an unsubstituted (C₃-C₄) alkenyl group, an unsubstituted (C₃-C₄) alkynyl group, a benzyl group; or a (C₁-C₄)alkyl group substituted with 2-methoxyethyl, 2-methylthioethyl, 2(ethoxycarbonyl)ethyl, or 1-(ethoxycarbonyl)ethyl;
$R^3$ is a (C₃-C₄) alkyl group;
Z' is a hydrogen atom;
Z" is a methyl group or an ethyl group; and
Y and Y' are independently hydrogen, methyl, chloro, cyano, methoxy, methylthio, acetyl or phenoxy.

12. A compound according to claim 11 having the formula

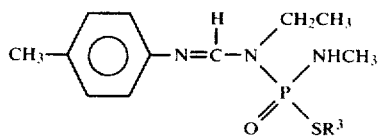

wherein $R^3$ is C₃H₇-n, C₄H₉-sec, or C₄H₉-iso.

13. A compound according to claim 11 having the formula

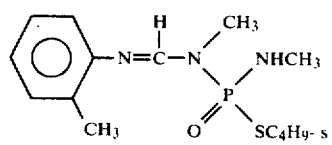

14. A compound according to claim 11 having the formula

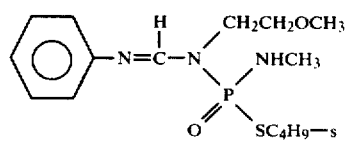

15. A compound according to claim 11 having the formula

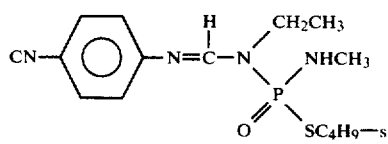

16. A compound according to claim 11 having the formula

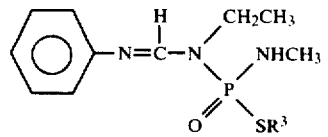

wherein $R^3$ is C₃H₇-n, C₄H₉-s, or C₄H₉-i.

17. A compound according to claim 11 having the formula

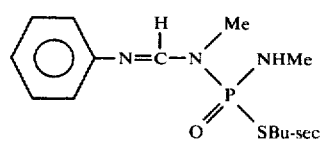

18. A compound according to claim 11 having the formula

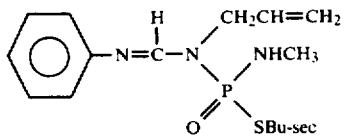

19. A compound according to claim 1 wherein $R^2$ is a group of the formula NZ'Z" wherein
    Z' is hydrogen or $(C_1-C_6)$ alkyl, and
    Z" is hydrogen, $(C_1-C_6)$ alkyl or $(C_3-C_6)$ alkenyl.

20. A pesticidal composition comprising a pesticidally effective amount of a compound according to any of claims 2 to 16 and an agronomically acceptable carrier.

21. A method of controlling pests which comprises applying directly to the pests, to the loci to be freed of or protected from attack by such pests, or to another substrate or pesticidally effective amount of a composition of claim 20.

22. A method for controlling pests in plants through systemic pesticidal action which comprises applying a pesticidally effective amount of a composition of claim 20 to the growth medium.

23. A substrate prepared by the method of claim 21.

24. A method according to claim 21 wherein the pests are phytopathogenic fungi.

25. A method according to claim 21 wherein the pests are acarids.

26. A method according to claim 21 wherein the pests are insects.

27. A method according to claim 21 wherein the pests are nematodes.

* * * * *